United States Patent [19]

Klein

[11] Patent Number: 4,506,400
[45] Date of Patent: Mar. 26, 1985

[54] ELECTRICALLY OPERATED TOOTHBRUSH

[75] Inventor: Horst Klein, Kelkheim-Fischbach, Fed. Rep. of Germany

[73] Assignee: Blendax-Werke R. Schneider GmbH & Co., Fed. Rep. of Germany

[21] Appl. No.: 556,302

[22] Filed: Nov. 30, 1983

[30] Foreign Application Priority Data

Nov. 30, 1982 [DE] Fed. Rep. of Germany ....... 3244262

[51] Int. Cl.³ ............................................. A46B 13/02
[52] U.S. Cl. ...................................... 15/22 R; 74/48; 74/837
[58] Field of Search ............................. 15/22 R, 22 C; 74/47–50, 70, 837; 51/170 R

[56] References Cited

U.S. PATENT DOCUMENTS 4,326,314  4/1982  Moret et al. ......................... 15/22 R

FOREIGN PATENT DOCUMENTS 1532781  3/1970  Fed. Rep. of Germany .
2944391  6/1980  Fed. Rep. of Germany .
2940275  4/1981  Fed. Rep. of Germany .

Primary Examiner—Edward L. Roberts
Attorney, Agent, or Firm—Connolly and Hutz

[57] ABSTRACT

The invention relates to an electrically operated toothbrush with oscillating motion, whose angle of oscillation can be adjusted.

This is a easily achieved by the fact that the rotation of the electric motor producing the motion can be reversed by pole changing, and thereby the radius of the circular orbit of the bolt of a rotating shaft connected to the holder taking up the slip-on brush in a curve-like opening of a free disc is changed in its dimension, thus producing a variation of the angular deflection of the rotating shaft.

4 Claims, 2 Drawing Figures

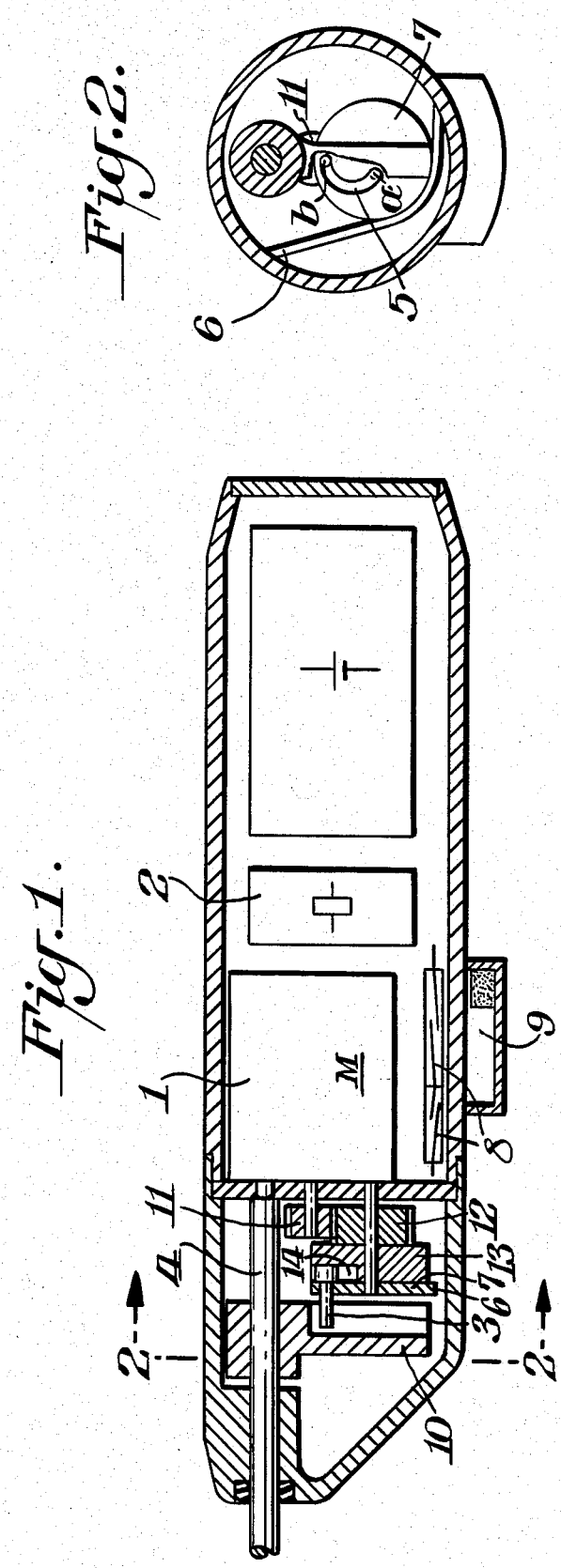

ELECTRICALLY OPERATED TOOTHBRUSH

The present invention relates to an electrically operated oscillating toothbrush having an adjustable amplitude of oscillation.

Electrically operated toothbrushes with oscillatory motion are already known and are successfully being used for cleaning the teeth. The oscillatory motion is achieved by converting a rotational motion of an electric motor with the help of a motion converter. Normally the oscillatory motion takes place within a constant oscillating amplitude which is transmitted by a shaft holder to the toothbrush fixed on this shaft.

It has already been suggested to design electrically operated toothbrushes with an oscillatory movement whose amplitude of oscillation may be adjusted to adapt it to the individual needs of the toothbrush user.

From German Offenlegungsschrift No. 1,532,781, a motor-operated toothbrush is known with a crank gear to produce an oscillatory motion on the brush whereby the amplitude of oscillation is adjustable by switching a working point of the crank gear elements which are connected to one another.

Due to their complicated mode of operation and the expensive construction mechanism electrical toothbrushes of this type are not being used in practice.

German Offenlegungsschrift No. 2,940,275 discloses an electrically operated toothbrush where the intensity of the oscillatory motion may be reduced.

Definitely, this problem is solved through a device where the amplitude of oscillation is reduced by increasing the distance between the axis of the electric motor and the axis of the brush with the electro-motoric drive of the brush via a crank guide or by regulating the intensity of the oscillatory motion by introduction of a resistor into the circuit of the electric drive.

Such a device also requires the use of further constructive features which cause a relatively complicated mode of action of the brush.

A further proposal for the variation of the amplitude of oscillation of an oscillating electrical toothbrush which is used in practice is described in German Offenlegungsschrift No. 2,944,391.

By means of an eccentric pin, which is fixed to a rotating carrier which is operated by an electric motor, and with an elongated slot provided on the inside of the toothbrush holder, which essentially extends radially to the longitudinal axis of the instrumental holder and in which the eccentric pin gears freely adjustable, the radial distance between the axis of rotation of the carrier of the eccentric pin and its gearing place in the elongated slot is changed, whereby an adjustment of the amplitude of oscillation can be effected.

Although this device shows considerable advantages in comparison to the prior art described above, it still has a relatively complicated construction which is susceptible to disturbances.

Moreover, by this construction—implying an acceptable maximum diameter for the handle of the electrical toothbrush—only a maximal amplitude deflection of approximately 30° is obtained, whereas it seems to be desirable to have a higher margin of variability to adjust the amplitude of oscillation.

Thus, it is an object of the invention, to design an electrical toothbrush having an adjustable amplitude of oscillation, being of relatively simple construction, operating without susceptibility to disturbances, and not having the disadvantages of the electrical toothbrushes known from the prior art mentioned above.

It has now been found that this problem may be resolved by reversing by pole changing the rotating direction of the electric motor producing the motion. This change of the rotating direction of the motor causes, via a free running disc provided with an arcuate slot, a change of the radius of the circular orbit of the bolt of a rotating shaft, to which the axis of a holder is connected to take up the slip-on brush. In this constructively simple way the angular deflection of the rotating shaft can be adjusted, whereby the deflection of the slip-on brush on the outer end of the holder can be varied between approx. 15° and approx. 55°, preferably between approx. 20° and approx. 50°.

The present invention is illustrated in more detail by the FIGS. 1 and 2:

FIG. 1 is a schematic cross-section through the handle of an electrical toothbrush designed according to the invention; and FIG. 2 shows a cross-section according to the line 2—2 from FIG. 1.

According to FIG. 1, in a toothbrush case partially indicated, an electric motor (1) is housed, which may be fed directly by the electrical network, a transformer or a battery and/or an accumulator. The rotating motion of this electric motor may be reversed by pole changing through a relay (2), e.g. via two reed contacts (8) in combination with a two-phase magnetic device (9) for switching the contacts. A motor pinion (11) rotates a gear (12) fixedly connected to a carrier (13). A free running disc (7) is positioned on the same shaft as gear (12) and carrier (13). An arcuate shaped slot (5) is eccentrically milled into the disc (7) and a pin or bolt (3) extends through the slot. The pin (3) is connected to rotate with the carrier (13) and is free to slide in a radial slot (14) in the carrier. The pin (3) is also movable along the arcuate slot (5) in the disc. When the motor is running, the pin (3) moves up and down in a slot in the lever (10) and thus transforms the rotational movement of the motor into a swinging movement which is translated to a toothbrush on shaft (4) via the lever (10) connected to the shaft.

The overall purpose of the invention herein is to create two different swing angles for the toothbrush slipped onto the shaft (4). As viewed in FIG. 2, when the motor (1) rotates in a clockwise direction, the carrier (13) moves in a counterclockwise direction whereby the pin (3) shifts to the inner end of the arcuate slot (5) to position (a) illustrated in FIG. 2. Due to the small radius from the center of rotation of carrier (13) to the center of the pin (3), the resultant circular orbit or path of pin (3) produces a swing of the lever (10) having a small amplitude. Conversely when the motor (1) is reversed to rotate in a counterclockwise direction, the carrier (13) rotates clockwise which positions the pin (3) at the outer end of the arcuate slot (5) shown as position (b) in FIG. 2. Such positioning produces a larger radius between the centers of carrier (13) and the pin (3) which in turn produces a greater circular orbit of pin (3) and a lever swing having a greater amplitude.

A spring (6) provides a light braking action on disc (7) which allows the pin (3) to slide between its positions at the ends of the arcuate slot (5) when the rotational direction of the motor is changed via the magnet (9) and the reed switches (8).

In this way, it is possible by means of a simple construction to cause angular deflections of the toothbrush between approx. 15° and approx. 55°, preferably between approx. 20° and approx. 50°.

I claim:

1. An electric toothbrush comprising a reversible electric motor with means to reverse the motor, a rotatable toothbrush holder with a lever secured thereto having a radial slot therein, and means interconnecting the lever with the electric motor for oscillating the lever and the toothbrush holder, the means including a radially slidable pin connected to rotate with the motor, the pin having a variable circular orbit and a free end positioned in the lever slot to oscillate the lever and toothbrush holder as the pin rotates about its circular orbit, and means to radially shift the pin when the motor is reversed to thereby vary the circular orbit of the pin which in turn varies the amplitude of oscillation of the lever and toothbrush holder.

2. An electric toothbrush as in claim 1 wherein the means to radially shift the pin includes a free running disc having an arcuate slot therein through which the pin extends, the slot having an inner end near the center of rotation of the pin and an outer end away from such center whereby the pin has a variable circular orbit depending upon its position at either end of the arcuate slot.

3. An electric toothbrush as in claim 2 including spring means connected to apply a light braking action to the free running disc.

4. An electric toothbrush as in claim 1 including a relay connected to change the pole commutation to reverse the electric motor.

* * * * *